(12) United States Patent
Reed

(10) Patent No.: US 9,011,504 B2
(45) Date of Patent: Apr. 21, 2015

(54) APPARATUS AND METHOD FOR USE IN THE TREATMENT OF HAMMERTOE

(76) Inventor: Gary Reed, Turlock, CA (US)

( * ) Notice: Subject to any disclaimer, the term of this patent is extended or adjusted under 35 U.S.C. 154(b) by 786 days.

(21) Appl. No.: 12/572,882

(22) Filed: Oct. 2, 2009

(65) Prior Publication Data

US 2011/0082508 A1    Apr. 7, 2011

(51) Int. Cl.

| A61B 17/86 | (2006.01) |
|---|---|
| A61B 17/72 | (2006.01) |
| A61F 2/42 | (2006.01) |
| A61F 2/30 | (2006.01) |

(52) U.S. Cl.
CPC ......... *A61B 17/8685* (2013.01); *A61B 17/7225* (2013.01); *A61B 17/7291* (2013.01); *A61F 2/4225* (2013.01); *A61F 2002/30235* (2013.01); *A61F 2002/30622* (2013.01); *A61F 2002/30772* (2013.01); *A61F 2002/3085* (2013.01); *A61F 2002/423* (2013.01); *A61F 2230/0069* (2013.01)

(58) Field of Classification Search
USPC ............ 606/65, 66, 300–321, 323, 325, 328, 606/329, 331; 623/21.11, 21.15, 21.19, 623/23.45, 23.47
See application file for complete search history.

(56) References Cited

U.S. PATENT DOCUMENTS

| 4,854,311 | A  | * | 8/1989 | Steffee | 606/66 |
|---|---|---|---|---|---|
| 5,498,265 | A  | * | 3/1996 | Asnis et al. | 606/916 |
| 6,517,543 | B1 | * | 2/2003 | Berrevoets et al. | 606/304 |
| 2004/0015172 | A1 | * | 1/2004 | Biedermann et al. | 606/73 |
| 2005/0038438 | A1 | * | 2/2005 | Anderson et al. | 606/73 |
| 2005/0143735 | A1 | * | 6/2005 | Kyle | 606/60 |

* cited by examiner

*Primary Examiner* — Michael T Schaper
(74) *Attorney, Agent, or Firm* — Majesty Law Group; Bernhard Kreten; Priscilla Fussell

(57) ABSTRACT

The apparatus and method is directed to a pair of self-tapping, interconnecting, externally and internally threaded devices that, when installed between two separate pieces of material, will draw and hold the material together as a single threaded unit. While the pair of threaded devices are being fastened into the host material, due to the unique design of their threads, no radial outward forces are produced that could cause cracking or splitting of the sections of the material into which they are installed. The external threads are helically defined into the exterior of each half of the device with a right hand thread defined into one half and a left hand thread into the other half. When the two halves are being fastened together, the increased thread pitch on one of the halves continuously draws the halves into each other even when the internal threads have already been maximally tightened.

3 Claims, 4 Drawing Sheets

APPARATUS AND METHOD FOR USE IN THE TREATMENT OF HAMMERTOE

BACKGROUND OF THE INVENTION

1. Field of the Invention

The invention relates to the field of orthopedics, and more particularly to a bone pin for the coupling of two separate pieces of bone together for use in the surgical correction of hammer toe.

2. Description of the Prior Art

One surgical method of treatment of hammertoe involves the surgical implantation of bone pins, and more particularly, an interphalangeal fusion pin which provides an anatomically correct angle between a first phalange and a second phalange, such as the proximal phalange and the intermediate phalange which exists at the proximal interphalangeal joint, wherein the pin is comprised of a resorbable or permanent material.

Digital deformities of the fingers and toes are some of the most common conditions encountered by orthopedists and podiatrists. Patients with digital deformities often experience significant pain from structural abnormalities. Some of these abnormalities are acquired, caused by traumatic injuries, neuromuscular pathologies, systemic diseases, or mechanical problems secondary to extrinsic pressures. The deformities are popularly known as either mallet finger, jersey finger, coach's finger, hammer toe, as well as a host of others indicative of several different pathologies.

Hammer toe is generally described in the medical literature as an acquired disorder, typically characterized by hyperextension of the metatarsophalangeal joint (MTPJ), hyperflexion of the proximal interphalangeal joint (PIPJ), and hyperextension of the distal interphalangeal joint (DIPJ). Although this condition can be conservatively managed (e.g., through the use of orthotic devices), in certain instances surgical intervention is required.

In order to prevent recurrence of the deformity and ensure the success of the surgical procedure, a proximal interphalangeal (PIP) joint arthrodesis is typically performed. The "end-to-end" or "peg-in-hole" techniques are the most commonly used procedures. The PIPJ is aligned with the rest of the toe in a corrected anatomical position and maintained in place by the use of a 0.045 Kirschner wire (K-wire) which is driven across the joint. Initially, the wire is placed from the PIPJ through the tip of the toe. It is then driven in retrograde fashion into the proximal phalanx. The exposed wire exiting the toe is bent to an angle greater than 90 degrees, and the bent portion is cut at 1 cm from the bend. At the conclusion of the surgical procedure, a small compressive dressing is placed around the toe, with a Jones compression splint being used for three to four weeks to protect the pin and the toe in order to maintain correction. The K-wire and the Jones splint are generally removed three weeks after surgery. Similar procedures may be followed to create arthrodesis of the distal interphalangeal joint (DIP) of the toe or for arthrodesis performed in the finger to correct digital abnormalities of the hand.

Although this type of surgical procedure has alleviated the discomfort of hammer toe and other abnormalities of the toe and finger joints for countless patients, the use of K-wire can result in the possible post-surgical misalignment of the phalanges (e.g., caused by distraction of the K-wire), as well as swelling, inflammation, and possible infection at the site of the exposed K-wire segment.

Of recent interest in the treatment of toe deformities, such as hammer toe, are prosthetic devices which have been used to treat deformities of the finger joints. For example, these devices can be inserted into adjoining phalanges of the finger and can serve to function ostensibly as a normal knuckle would. Because it is generally necessary to permit one or more of the joints of the finger to flex and bend, some of these devices are slightly angled to provide for an anatomically acceptable interphalangeal joint angle of the finger. Furthermore, some of these devices allow the joint portion to bend to a significant degree, thus permitting the finger a relatively wide range of articulation.

These devices are typically comprised of metallic or thermoplastic materials which, while being biocompatible, are also physiologically inert and thus are not resorbed by the body. There are, however, conditions in which an arthrodesis, or fusing of the affected finger or toe joint is desired, making a permanent device which is designed to permit joint flexion/extension inappropriate. Thus, the use of these permanent prosthetic devices in the treatment of hammer toe and other digital deformities, wherein the goal of the operation is arthrodesis, whereby the presence of the device would only be required for a short number of weeks to aid in maintaining correct anatomical alignment of the phalanges for fusion, would not be indicated. Additionally, these permanent devices would also be contraindicated in the treatment of certain finger conditions where the phalanges need to be correctly anatomically aligned for only a few weeks until a proper amount of healing for fusion has occurred.

BRIEF SUMMARY OF THE INVENTION

The illustrated embodiments of the disclosed apparatus and method is directed to a pair of self-tapping, interconnecting, externally and internally threaded cylindrical bone pin halves that when installed between two separate pieces of material or bone, will draw and hold the bone together as a single unit. The pin halves have an axial bore defined therethrough. One half with internal threading defined in the bore and mating external threading defined into a exterior surface of a male peg from the other half. The two halves are threaded together by means of mating internal threading and the external threading on the male peg. While the pair of threaded pin halves are being fastened into the host material or bone, due to the unique design of their external threads no radial outward forces are produced that could cause cracking or splitting of the sections of the bone into which they are implanted. The external threads are defined into the exterior surface of each half of the pin, one half with a right hand thread and the other half with a left hand thread. When the two halves are joined together, the increased thread pitch on one of the halves continuously draws bone segments into which the halves have been implanted into each other even when the internal threads of each half have already been fully tightened.

The current device also comprises interlocking hook self-tapping threads which provide sharp and efficient cutting edges for self-tapping into the host material. Repository spaces are present in each of the device halves for collecting all of the chips created in the tapping process.

Another component of the current device is the adjustable drawing capability of the opposing halves of the device. The opposing force creates a clamping load that secures the bone pin immediately and permanently into the host material or bone. The combination of the interlocking hook threads and the opposing pressure flanks of each half of the bone pin together form the perfect thread engagement, producing a strong and durable connection between the two halves.

The interlocking external threads of the device mechanically join with the surrounding host material or bone segments when the two halves are assembled and tightened together. When used in bone, this interlocking function promotes bone regeneration for faster healing due to the unique load bearing capability and the ability to draw the mating ends of the bone tightly together and hold them firmly. This is the single most important factor in promoting rapid bone remodeling and shortening the post-operative recovery period.

In a simple and effective way, the disclosed thread design creates an instant interlocking threaded union, excellent uniform axial load-bearing capability, and very good resistance to vertical shear and bending loads. The unique interlocking hook thread prevents radial outward spreading forces from occurring when the device is tightened and or loaded. The device can also be easily removed and reinstalled if needed.

While the following description will describe an apparatus and method for inserting the current device into bone, and more specifically to treat the medical condition known commonly as hammer toe, it is to be expressly understood that the current device may be used for any similar type of medical procedure without departing from the original spirit and scope of the invention. Similarly, it is to be expressly understood that the current device may be installed in other host materials such as wood, plastic, metal, or any other material now known or later devised in order to couple two separate pieces of the said host material together.

More formally, the illustrated embodiment of the invention includes an apparatus for coupling at least two pieces of host material together, such as two phlanges in a hammer toe, comprising: a hollow proximal half with an internal surface and an external surface for implantation into one of the two pieces of the host material; a hollow distal half with an internal surface and an external surface for implantation into the other one of the two pieces of host material; and threading for threadably engaging the distal half and proximal half together.

The proximal half and the distal half each comprise a helical external thread the external surface of each respective half for engagement with the two pieces of host material.

The proximal half and the distal half each comprise at least two opposing self-tapping bores defined through the internal and external surfaces and the external threads of each respective half to act as a repository for the removed debris of the host material.

The external threads on the proximal half are arranged and configured in the opposite helical sense to that of the external threads on the distal half.

The threading for threadably engaging the distal half and proximal half together comprise: a peg comprising a male threaded portion disposed on a distal end of the proximal half; and a female threaded portion defined on the internal surface of the distal half.

The proximal half and the distal half both comprise a hexagonally shaped internal bore defined in at least a portion of each respective half.

The apparatus distal half further comprises at least two opposing wrench flats defined on the external surface.

The external threads on the proximal half are orientated at a different pitch to that of the external threads on the distal half.

The external threads that have the at least two self-tapping bores defined therethrough comprise sharp, angled open faces to cut into the host material when the proximal half and distal half are rotated.

The illustrated embodiment of the invention also includes a method for coupling at least two pieces of host material together, such as two phlanges of a hammer toe, with an adjustable device comprising the steps of: inserting a proximal half of the device into a proximal one of the two pieces of the host material; inserting a distal half of the device into a distal one of the two pieces of the host material; and coupling the proximal one of the two pieces of the host material to the distal one of the two pieces of the host material by means of the proximal half of the device.

The step of inserting the proximal half of the device in the proximal one of the two pieces of the host material comprises the steps of: rotating the proximal half of the device into a predrilled bore; cutting a female thread into the predrilled bore in the host material by means of an external thread disposed around the proximal half of the device; and engaging the female thread cut into the host material by means of the external thread disposed around the proximal half of the device.

The step of inserting the distal half of the device in the distal one of the two pieces of the host material comprises the steps of: rotating the distal half of the device into a predrilled bore; cutting a female thread into the predrilled bore in the host material by means of an external thread disposed around the distal half of the device; and engaging the female thread cut into the host material by means of the external thread disposed around the distal half of the device.

The method further comprises the steps of collecting any debris from the host material in a repository defined into each of the proximal and distal halves of the device when each respective device half is being inserted into its respective one of the two pieces of the host material.

The step of coupling the proximal portion of the host material to the distal one of the two pieces of the host material by means of the proximal half of the device and the distal half of the device inserted into each respective one of the two pieces of the host material comprises the steps of: disposing or sliding the distal half of the device over a male peg disposed on the distal end of the proximal half of the device; rotating the distal half of the device about the male peg disposed on the distal end of the proximal half of the device; and engaging a female threaded portion defined in an interior surface of the distal half of the device to a male thread portion disposed on the male peg of the proximal half of the device.

The step of rotating the distal half of the device about the male peg disposed on the distal end of the proximal half of the device comprises the steps of: inserting a hex shaped driving tool into a distal end of the distal half of the device; engaging the hex shaped driving tool in a hexagonally shaped interior bore of the distal half of the device; and rotating the hex shaped driving tool.

The method further comprises the step of adjusting the distance between the proximal one of the two pieces of the host material and the distal one of the two pieces of the host material by means of rotating the distal and proximal halves of the device after they have been joined together.

The step of rotating the distal half of the device comprises the steps of: inserting a hex shaped driving tool into a distal end of the distal half of the device; engaging the hex shaped driving tool in a hexagonally shaped interior bore of the distal half of the device; and rotating the hex shaped driving tool.

The illustrated embodiment of the invention still further includes a method for coupling at least two pieces of host material together, such as adjacent phlanges of a hammer toe, with an adjustable device comprising the steps of: inserting a proximal half of the device into a proximal one of the two pieces of the host material; inserting a distal half of the device into a distal one of the two pieces of the host material; coupling the proximal one of the two pieces of the host material to the distal one of the two pieces of the host material by means of the proximal half of the device and the distal half of the device which has been inserted into each respective one of the two pieces of the host material; collecting any debris from the host material in a repository defined into each of the proximal and distal halves of the device when each respective device half is being inserted into its respective one of the two pieces of the host material; and adjusting the distance between the proximal one of the two pieces of the host material and the distal one of the two pieces of the host material by means of rotating the distal half of the device after it has been jointed to the proximal half of the device.

The step of inserting the proximal half of the device in the proximal one to the two pieces of the host material and inserting the distal half of the device in the distal one to the two pieces of the host material comprises the steps of: rotating each of the proximal and distal halves of the device; cutting a female thread into each respective one to the two pieces of the host material by means of an external thread disposed around each of the proximal and distal halves of the device; and engaging the female thread in the host material by means of the external thread disposed around each of the proximal and distal halves of the device.

The step of rotating of each of the proximal and distal halves of the device comprises the steps of: inserting a hex shaped driving tool into each of the distal ends of the distal and proximal halves of the device respectively; engaging each hex shaped driving tool in a hexagonally shaped interior bore in each of the distal and proximal halves of the device respectively; and rotating each hex shaped driving tool.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
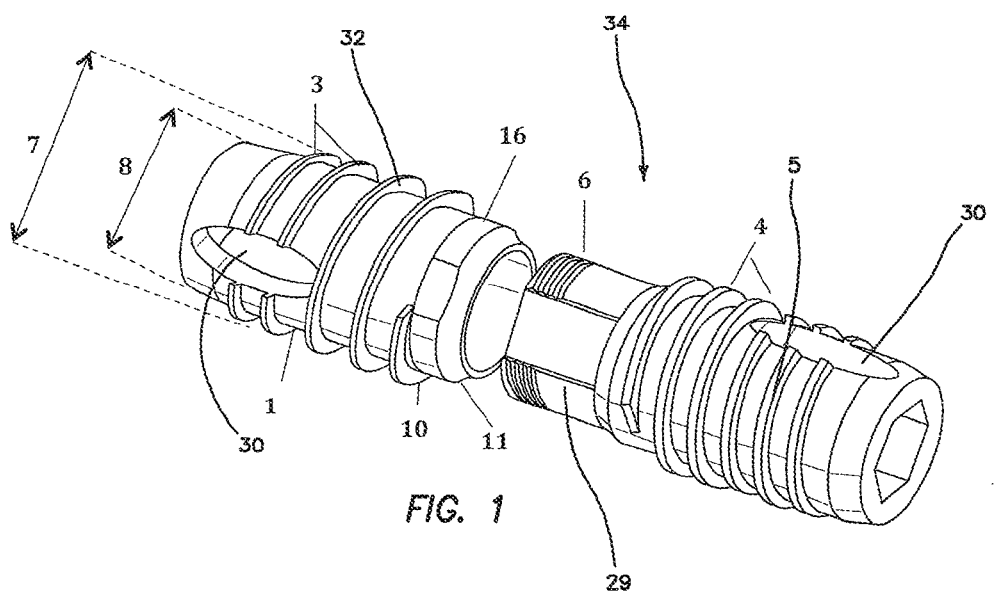
FIG. 1 is an exploded view of the threaded device depicting both the distal and proximal portions of the threaded device.

Turning now to FIG. 1, a distal half 1 and a proximal half 5 of the bone pin 34 are shown. As described below distal half 1 is implanted in the distal phlange and proximal half 5 is implanted into the proximal phlange of a hammer toe joint. Both halves 1, 5 are generally cylindrical with a longitudinal bore define therethrough on the longitudinal axis of each half. The distal half 1 includes an external helical thread 3 defined into the exterior surface of the distal half 1. The tooth 32 of the external helical thread 3 is defined between a minor diameter 8 and a major diameter 7. Similarly, an external helical thread 4 is also defined into the exterior surface of the proximal half 5, however the external thread 3 of the distal half 1 has a greater pitch than that of the threads 4 of the proximal half 5. The proximal half 5 further comprises a male peg 29 on its distal end. An external helical thread 6 is defined into the exterior surface of the male peg 29. A mating internal female thread 10 is defined into a bore 11 of the proximal end of the distal half 1.

Both the distal and proximal halves 1, 5 include at least a pair of diametrically opposed tapping bores 30 perpendicularly defined through the cylindrical surface and perpendicular to the longitudinal axis of each half. The tapping bores 30 are preferably oval shaped and are defined on opposing sides through the threads 3, 4 of each of the halves 1, 5 respectively, however other shapes or other configurations may be used without departing from the original spirit and scope of the invention. The tapping bores 30 are defined with very sharp cutting edges through the thread 3, 4 to enable the threads 3, 4 to become self-tapping. The perpendicular bores 30 also serve as a repository for the bone chips created during the thread cutting process. This allows the chips to be moved into and contained within the perpendicular bore 30 in each half 1, 5 thereby preventing galling, interference and radial forces during the thread cutting process. This produces clean cut threads within the friable bone or other host material similar to those cut with a tap, but unlike the imperfect threads cut by the crude and dull edges of prior art self-tapping devices.

Figure 2:
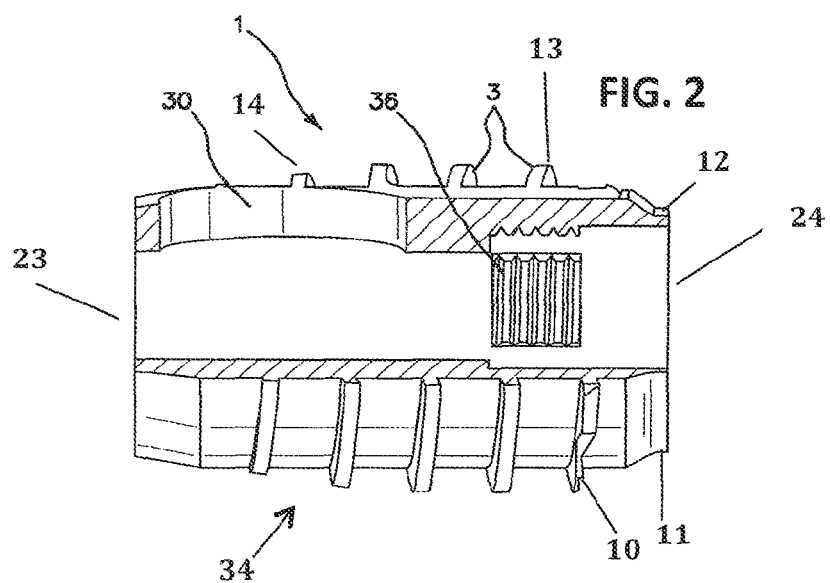
FIG. 2 is a partially cutaway cross-sectional view of the distal portion of the threaded device shown in FIG. 1.

The internal components of the distal half 1 of the current device can been seen in the partially cutaway cross-sectional view of FIG. 2. The distal half 1 has an internal bore 11 with a smooth portion for receiving peg 29 and followed by a threaded portion carrying mating threads 10, which bore 11 extends from the proximal end 24 of the distal half 1 to an internal hexagonally shaped bore 12. Internal female quick lock thread 10 is defined within a portion of the smooth internal surface 11. The internal hexagonally shaped bore 12 is disposed along the longitudinal axis of the distal half 1 and extends to distal end 23 of the distal half 1.

Also seen in FIG. 2 is the orientation of the external threads 3 in relation to the longitudinal axis of the distal half 1. Those external threads 3 located proximally of the tapping bores 30 are leading tooth flanks 13, and those external threads 3 through which tapping bores 30 are defined are trailing tooth flanks 14. The leading tooth flanks 13 are orientated at less than a 90 degree angle from the longitudinal axis of the distal half 1. The trailing tooth flanks 14 are orientated at an angle between 90 and 95 degrees relative to the longitudinal axis of the distal half 1. The recited angles of the leading and trailing tooth flanks 13, 14, when engaged in a host material or bone, help produce an interlocking mechanical grip on the host material or bone. The trailing tooth flanks 14, unlike the leading tooth flanks 13, are open faced due to the oval shaped tapping bores 30 being defined through them. This configuration results in the trailing tooth flanks 14 having a sharp, angled edge, which when rotated about the longitudinal axis will cut into the surrounding bone or host material and thus render bone pin 34 self-tapping.

Figure 3:
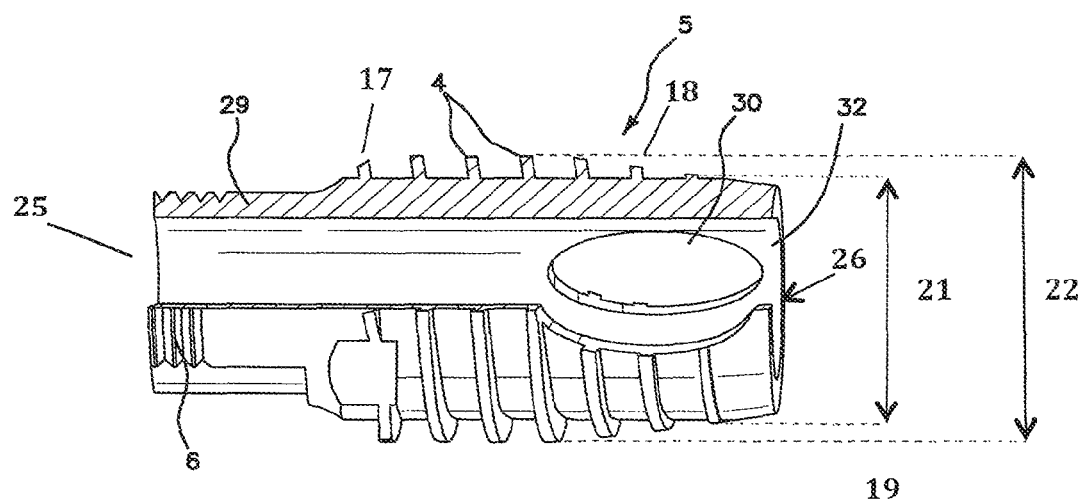
FIG. 3 is a partially cutaway cross-sectional view of the proximal portion of the threaded device shown in FIG. 1.

The corresponding internal components of the proximal half 5 of the current device can be seen in FIG. 3. The proximal half 5 includes a smooth, hexagonally shaped internal bore 19 which extends from the proximal end 26 of the proximal half 5, to the distal end 25 of the proximal half 5. The external threads 4 helically disposed around the proximal half 5 have a major diameter 22 and a minor diameter 21. Those external threads 4 located distally with respect to the tapping bores 30 are leading tooth flanks 17, and those external threads 4 through which the tapping bores 30 are defined are trailing tooth flanks 18. The leading tooth flanks 17 are orientated at an angle 90 to 95 degrees relative to the longitudinal axis of the proximal half 5. The trailing tooth flanks 18 are orientated at an angle less than 90 degrees relative to the longitudinal axis of the proximal half 5. The recited angles of the leading and trailing tooth flanks 17, 18, when engaged in a host material or bone, help produce an interlocking mechanical grip on the host material or bone. The cutting faces of the thread teeth are open faced due to the oval shaped tapping bores 30 defined through them. This configuration results in the teeth faces having sharp, angled edges which when rotated about the longitudinal axis will cut into the surrounding bone or host material and thus enable the bone pin 34 to be self-tapping.

Currently, well established medical procedures teach that solid fixation of the toe joint to eliminate articulation is the most satisfactory solution for treating the common malady of hammer toe. The current device helps accomplish this procedure in a novel and improved way by being inserted between the proximal and distal phalanges of a patient.

Figure 4:
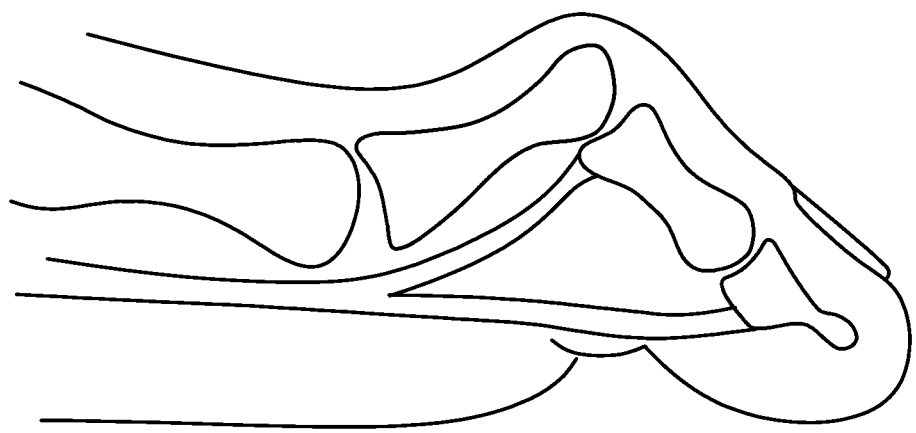
FIG. 4 is a side cross-sectional view of a hammer toe in which the illustrated embodiment of the invention is employed.
Figure 5:
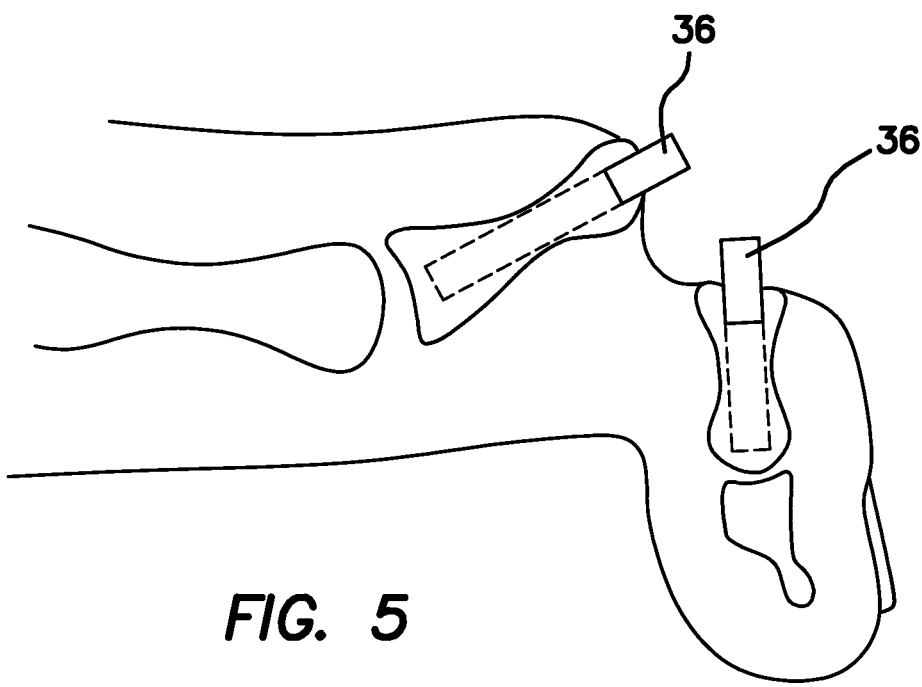
FIG. 5 is a side cross-sectional view of a hammer toe after the joint has been opened and guide pins inserted in preparation for drilling of a receiving bore into each of the opposing phlanges into which bores the halves of the bone pin of the illustrated embodiment will be implanted.
Figure 6:
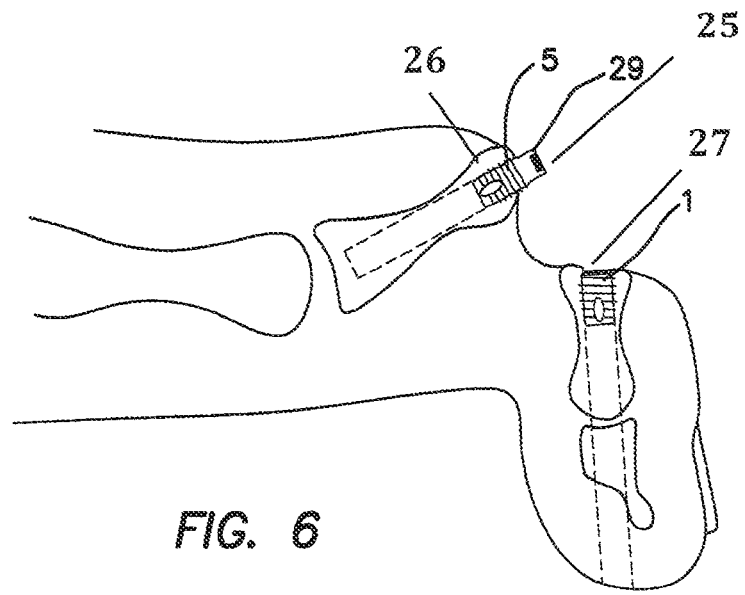
FIG. 6 is a side cross-sectional view of a hammer toe after the bone pin halves of the illustrated embodiment have been implanted, but before they have been joined together.

First, a surgeon or other medical professional opens the soft tissues of the patient's hammer toe as shown in FIG. 4 and then surgically partially separates the joint. The joint is then opened furthered by bending the partially disconnected distal phalanges downward to expose the proximal end of the bone as shown in cross-sectional view of FIG. 5. A guide pin hole is then drilled through the end of the proximal portion of the bone and then a guide pin 36 is then installed to help facilitate the use of a cannulated drill bit to further open the inside of the bone into a large enough cavity to accommodate the proximal half 5 of the bone pin 34.

The proximal end 26 of the proximal half 5 is inserted into the drilled hole in the proximal phlange. A hex shaped driving tool, commonly known in the art, is then inserted into the distal end 25 of the proximal half 5 and extended into the hexagonally shaped internal bore 19. The proximal half 5 is then screwed into the surrounding bone in the proximal phlange by rotating the hex shaped driving tool. As the proximal half 5 is being rotated, the open faced trailing tooth flanks 18 cut into the surface of the surrounding bone of the proximal phlange and allow the external threads 4 to dig deeper into the bone. Bone chips or any other refuse from the host material is removed by the external threads 4 and pushed into the oval shaped tapping bores 30 and out of the way of the self-tapping external threads 4, thus preventing galling and any unnecessary radial forces from being produced. As the proximal half 5 is rotated into the bone, the external threads 4 self-tap the proximal half 5 more deeply into the proximal phlange and more securely implant half 5 into the host material, until just the male peg 29 is left protruding beyond the end of the proximal phlange.

With the distal phalanges bent downward a second pilot hole is drilled into the proximal end of the bone of the distal phalanges entirely through to the distal end of the toe. An alignment pin is inserted into the pilot hole in the proximal end of the distal bone at the opened joint. The cannulated drill is inserted over the pin and used to increase the size of the pilot hole to a depth to allow insertion of the distal half 1 of the bone pin 34.

The distal end 23 of the distal half 1 is first inserted into the proximal end of the distal phlange and a hex shaped driving tool, commonly known in the art, is inserted into the proximal end 24 of the distal half 1. In order to be inserted correctly, the hex shaped driving tool extends past the internal female quick lock thread 10 and into the internal hexagonally shaped bore 12. Once the hex driving tool is in place, the distal half 3 is then rotated into the pilot hole in the same fashion as the proximal half 5. As the distal half 1 is being rotated, the open faced trailing tooth flanks 14 cut into the surface of the surrounding bone and allow the external threads 3 to dig deeper into the bone of the distal phlange. Bone chips or any other refuse from the host material is removed by the external threads 3 and pushed into the oval shaped tapping bores 30 and out of the way of the self-tapping external threads 3, thus preventing galling and any unnecessary radial forces from being produced. As the distal half 1 is rotated into the bone, the external threads 3 self-tap the distal half 1 more deeply into the bone and half 1 is more securely implanted into the bone, until just a fillet 27 defined on the proximal end 24 of the distal half 1 is left protruding beyond the proximal end of the bone of the distal phlange.

Figure 7:
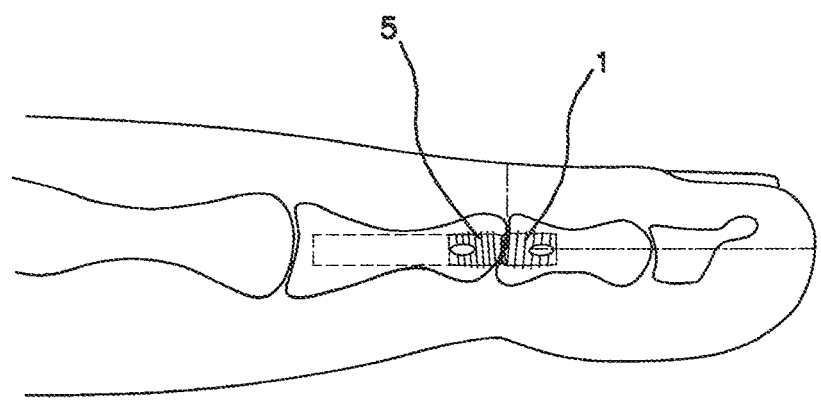
FIG. 7 is a side cross-sectional view of a hammer toe after the bone pin halves of the illustrated embodiment have joined together.

Holding the proximal phalange that contains the proximal half 5 in one hand, the surgeon pulls distal phalange containing the distal half 1 away slightly while rotating the distal phlange counterclockwise so that the proximal end 24 of the distal half 1 is installed over the distal end 25 of the proximal half 5, making sure that the male peg 29 is aligned with and inserted into the smooth inner bore 11 of the distal half 1. The distal half 1 may then be tightened and coupled to the proximal half 5 by either using a spanner wrench commonly known in the art interfaced with two opposing wrench flats 16 defined on the external surface of the distal half 1 as shown in FIG. 1, or by using a hex shaped wrench inserted through the drilled pilot hole at the distal end of the toe and into the distal end 23 of the distal half 1. In the latter instance the hex wrench is inserted into the internal hexagonally shaped bore 12 and then rotated. As the distal half 1 is being rotated, the external threads 6 on the male peg 29 of the proximal half 5 engage the internal female quick lock thread 10. The distal half 1 is rotated about the male peg 29 until the male peg 29 makes contact with the shoulder 36 at the proximal end of internal hexagonal bore 12 and further engagement with the internal female quick lock thread 10 is no longer possible. With the distal half 1 and proximal half 5 now firmly coupled together, the bone pin 34 comprised of halves 1 and 5 effectively becomes a single piece. The bone pin 34 is further rotated by the hex wrench in a clockwise direction, which due to the opposing left and right hand orientated threads of the distal half 1 and proximal half 5 as discussed above, cause the separated proximal and distal phalanges to be drawn together and further increase the stability and strength of the coupling of the bone pin 34. The distance between the phalanges can then be easily adjusted by rotation of the coupled proximal half 5 and distal half 1 in either a clockwise or counterclockwise direction as shown in FIG. 7.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for coupling two pieces of host material together, comprising: a distal half and a proximal half, each said half having a longitudinal axis which, when conjoined, couple respectively a first piece of host material to a second piece of host material along a now common longitudinal axis, said distal half having a thread pattern helically disposed on an exterior surface, wound in one direction, said proximal half having a thread pattern helically disposed on an exterior surface wound in a second direction, opposite from said distal half, means to removeably attach said distal and proximal halves together such that when united together, further rotation of either said proximal or distal half causes said halves to move one relative to the other until they are either dissociated or bound together, wherein said threads on said exterior surfaces each have a portion defining self-tapping threads located adjacent bores which pass through said exterior surfaces into interiors thereof, said self-tapping threads having tooth flanks on each half facing each other and defining an included angle relative to said longitudinal axes of said proximal and distal halves of less than 90 degrees, and each thread of said self-tapping threads has an opposite flank on each tooth with an included angle relative to said longitudinal axes of said proximal and distal halves greater than or equal to 90 degrees, wherein said means to removeably attach said distal and proximal halves together includes a peg projecting axially from said distal half and having a thread disposed at a terminus for threaded axial registry with a complementary formed thread disposed in said proximal half, wherein said means to removeably attach said halves further includes wrench flats disposed on an exterior surface of said peg.

2. The apparatus of claim 1 wherein said means to removeably attach said halves further includes a hexagonal bore formed in said halves.

3. The apparatus of claim 1 wherein said thread pattern on said distal half has a pitch different than that of said thread pattern on said proximal half.

* * * * *